(12) United States Patent
Lafont

(10) Patent No.: US 9,351,868 B2
(45) Date of Patent: May 31, 2016

(54) METHOD FOR MAKING A RESERVOIR CONTAINING AN ACTIVE SUBSTANCE DIFFUSED THROUGH THE RESERVOIR AND INSTALLATION THEREFOR

(71) Applicant: BAYER INTELLECTUAL PROPERTY GmbH, Monheim (DE)

(72) Inventor: Charles-Dominique Lafont, Cusset (FR)

(73) Assignee: Bayer Oy, Turku (FI)

( * ) Notice: Subject to any disclaimer, the term of this patent is extended or adjusted under 35 U.S.C. 154(b) by 0 days.

(21) Appl. No.: 13/784,384

(22) Filed: Mar. 4, 2013

(65) Prior Publication Data

US 2014/0076327 A1 Mar. 20, 2014

Related U.S. Application Data

(63) Continuation of application No. 11/795,262, filed as application No. PCT/FR2006/000159 on Jan. 24, 2006, now abandoned.

(30) Foreign Application Priority Data

Jan. 25, 2005 (FR) ..................... 05 00758

(51) Int. Cl.
*A61F 6/14* (2006.01)
(52) U.S. Cl.
CPC ....................... *A61F 6/14* (2013.01)
(58) Field of Classification Search
None
See application file for complete search history.

(56) References Cited

U.S. PATENT DOCUMENTS

| 4,920,727 | A | 5/1990 | Ristimaki et al. |
| 5,230,207 | A | 7/1993 | Hartzell et al. |
| 5,369,943 | A | 12/1994 | Helle et al. |
| 5,400,804 | A | 3/1995 | Helle et al. |
| 2006/0016451 | A1 | 1/2006 | Hallinen et al. |
| 2008/0095825 | A1 | 4/2008 | Lafont |

FOREIGN PATENT DOCUMENTS

| EP | 0652738 | 5/1995 |
| EP | 1400258 A1 | 3/2004 |
| WO | 9403144 A1 | 2/1994 |

OTHER PUBLICATIONS

Written Opinion for International Application No. PCT/FR2006/000159 (Translation), Jul. 31, 2007, 6 pages.
International Bureau of WIPO, International Preliminary Report on Patentability for International Patent Application No. PCT/FR2006/000159, Jul. 31, 2007, 7 pages.
European Patent Office, International Search Report for International Patent Application No. PCT/FR2006/000159, Sep. 21, 2006, 10 pages.
USPTO, Non-final Office Action for U.S. Appl. No. 11/795,262, Dec. 22, 2011, 10 pages.
USPTO, Restriction Requirement for U.S. Appl. No. 11/795,262, Sep. 13, 2011, 6 pages.
USPTO, Final Office Action for U.S. Appl. No. 11/795,262, Sep. 4, 2012, 8 pages.

*Primary Examiner* — Alicia L Otton
(74) *Attorney, Agent, or Firm* — Aseem Mehta

(57) ABSTRACT

The invention concerns a method for making a reservoir (5) containing an active substance and adapted to be introduced into a natural cavity of a living being, the reservoir (5) comprising a membrane (9) permeable to the active substance. Said method includes steps which consist in: a) placing at least one tube designed to constitute the membrane (9) in at least one retaining member, the ends of the tube being open; b) injecting through at least one of the tube ends, while expelling any residual air present in the tube, an amount of a product (8) containing an active substance in pasty form, said amount corresponding substantially to an inner free volume of the tube; c) when the tube is full, closing the end of the tube opposite the end from which the injection is performed; d) proceeding with the injection of the product (8) in pasty form into the free volume until achieving the outer desired diameter (D5) for the reservoir (5) by allowing the radial expansion of the tube; e) polymerizing the product (8) when the reservoir (5) reaches the desired outer diameter (D5) while maintaining the reservoir (6) in the retaining member. The method is particularly designed for producing hormonal intrauterine contraceptive devices.

5 Claims, 5 Drawing Sheets

Figure 11:
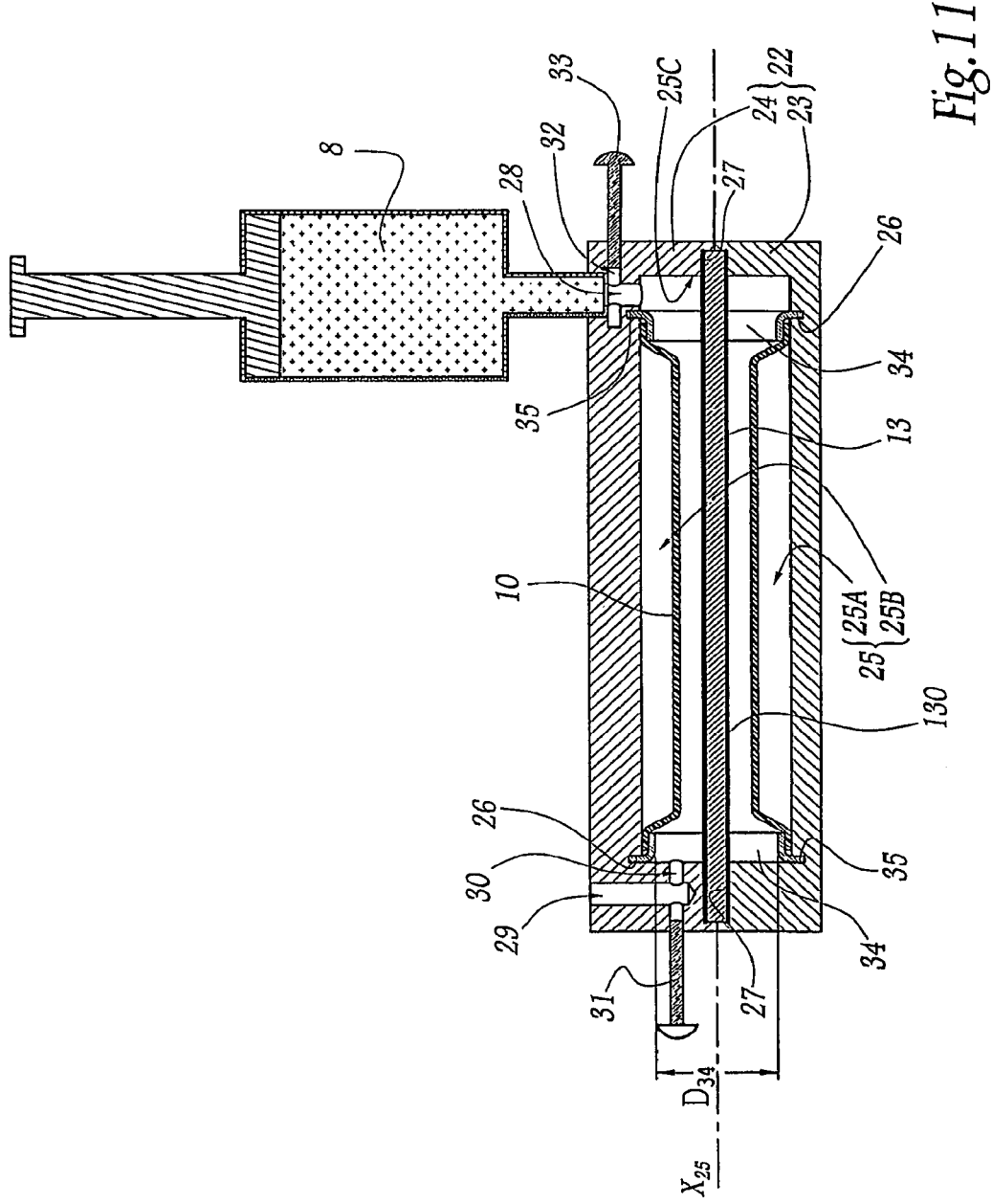

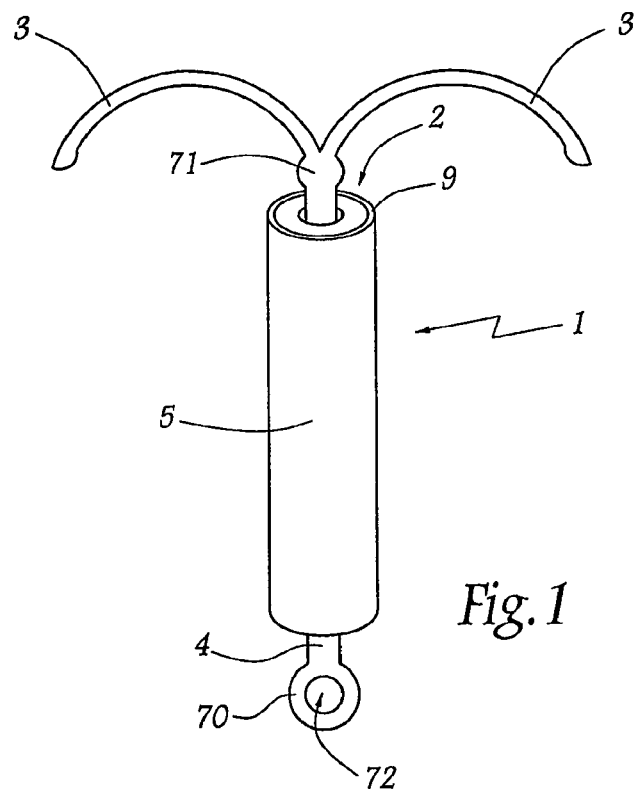
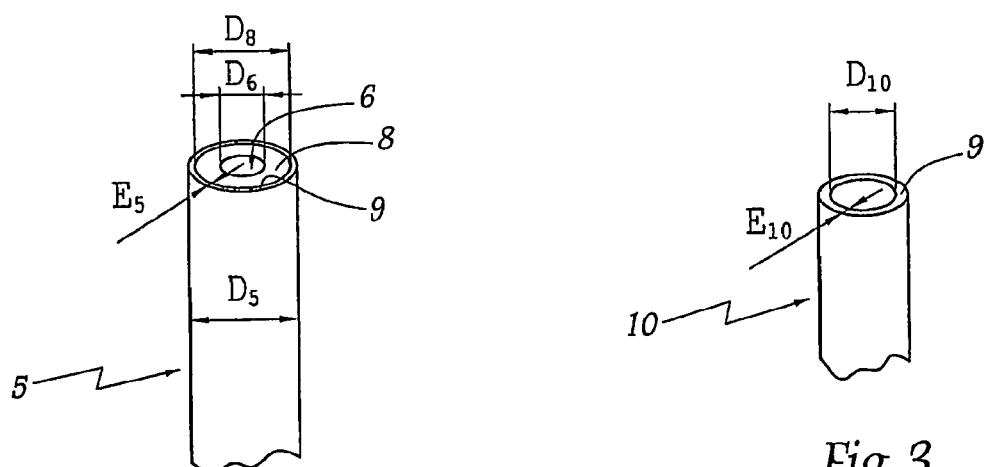

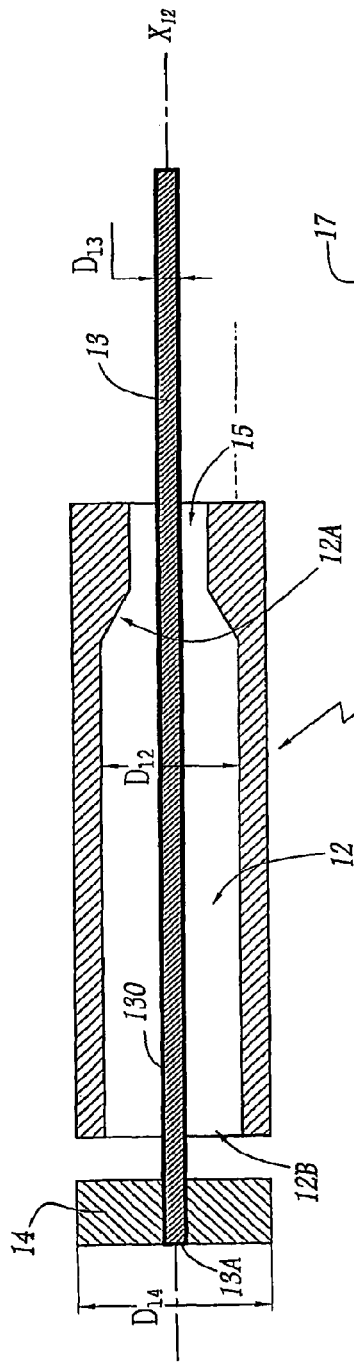
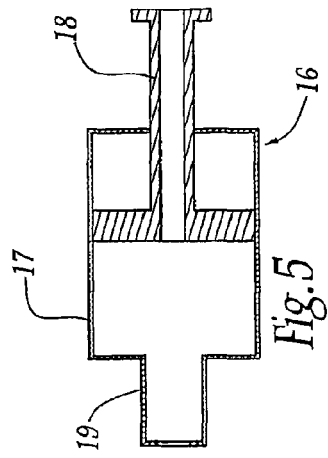
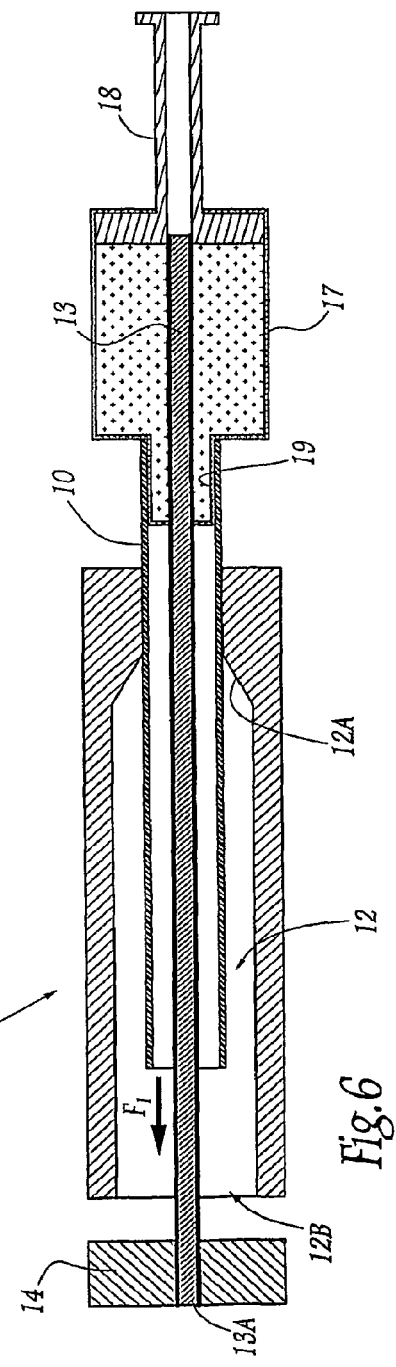
Fig.4
Fig.5
Fig.6

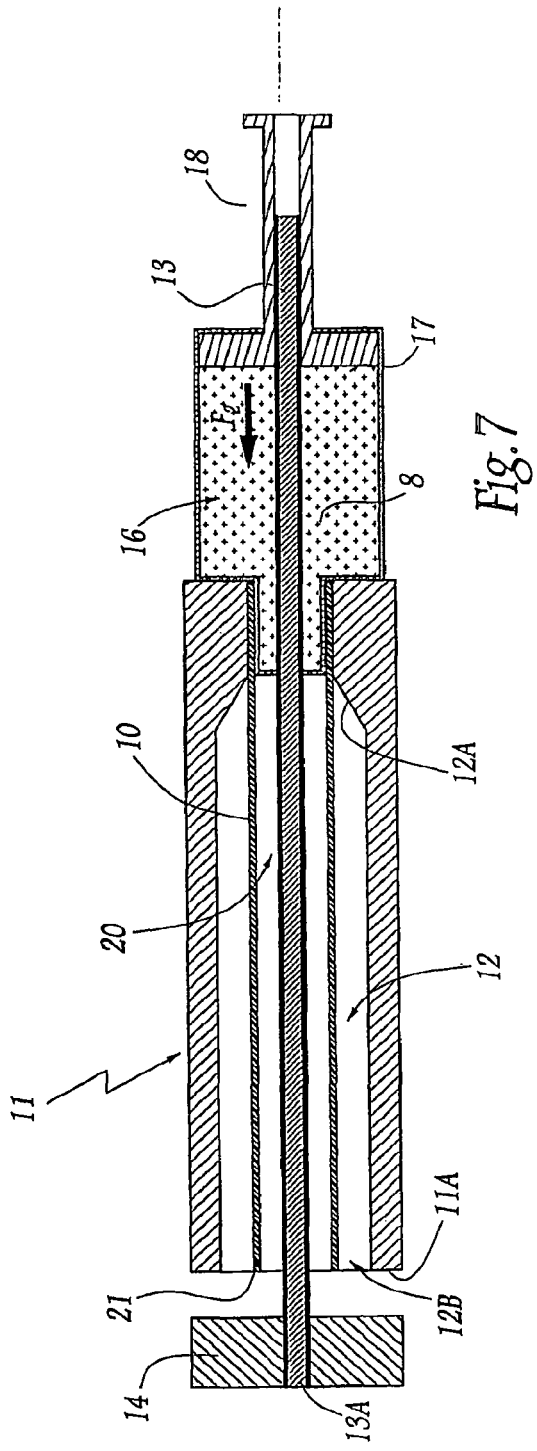
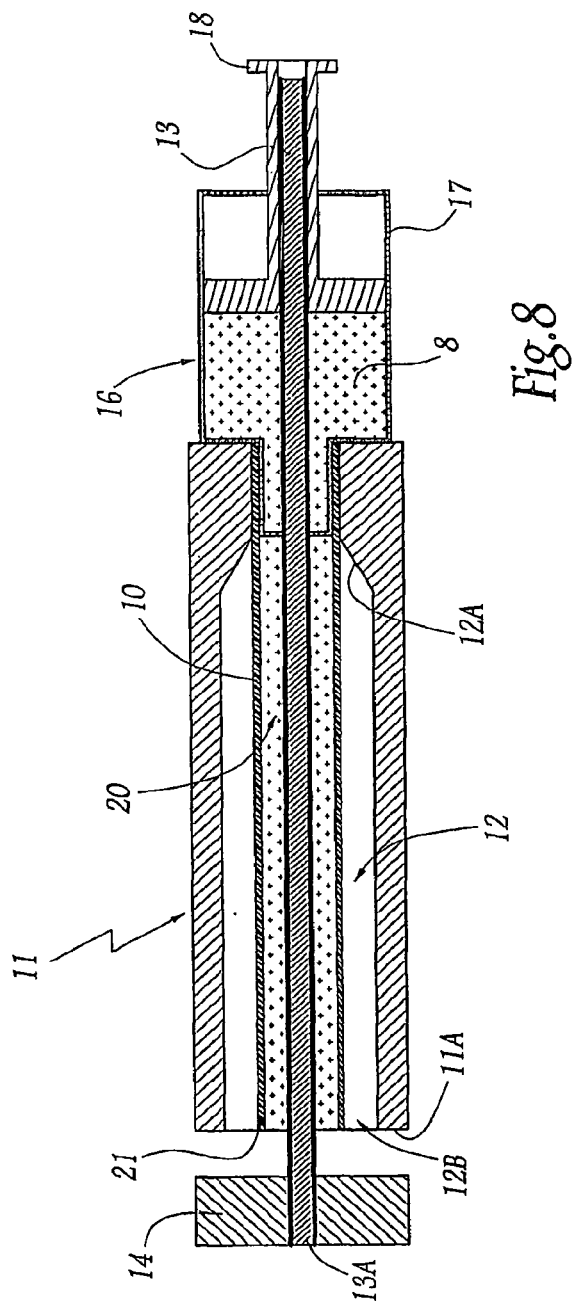

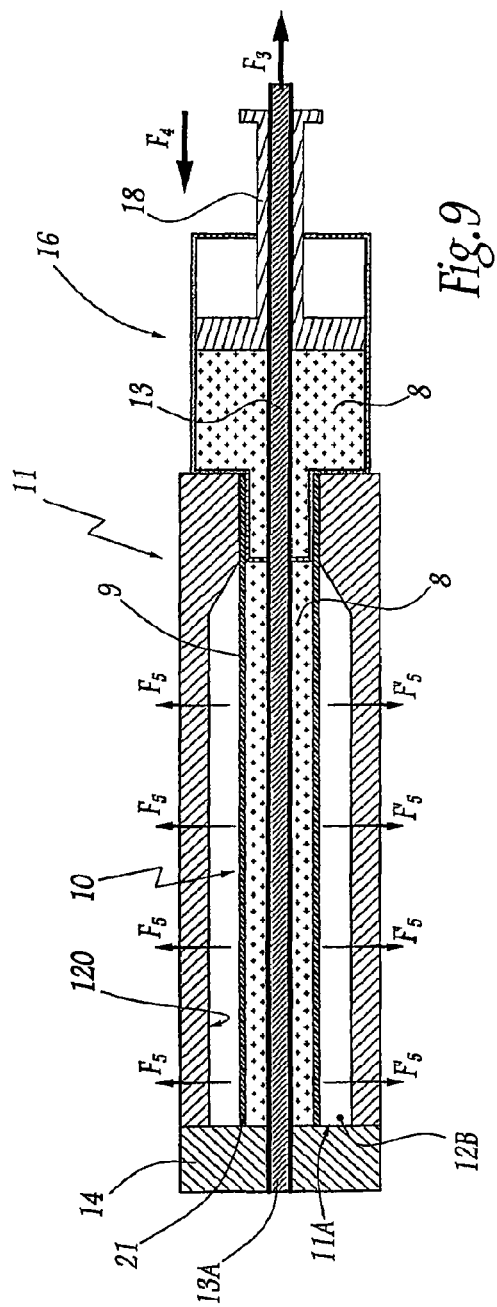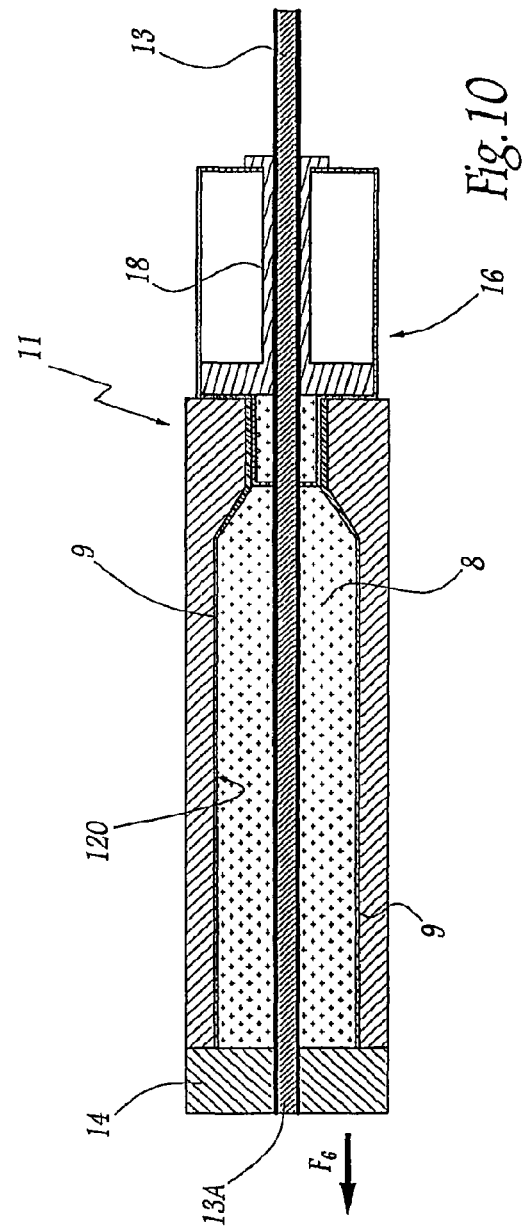

METHOD FOR MAKING A RESERVOIR CONTAINING AN ACTIVE SUBSTANCE DIFFUSED THROUGH THE RESERVOIR AND INSTALLATION THEREFOR

The invention relates to a method of producing a reservoir containing an active substance and suitable for being inserted into a natural cavity of a living being, this reservoir being enveloped by a membrane permeable to the active substance.

Such reservoirs are used as intrauterine contraceptive devices also called hormonal intrauterine devices. This type of reservoir comprises a tubular membrane, usually made of a silicone-based material. A product containing in particular a silicone-based matrix and a contraceptive hormone is enveloped by this membrane. The membrane is permeable to the hormone, the latter diffusing steadily from the inside of the reservoir toward the uterine cavity. Such intrauterine devices also comprise a polymer-based inert support, to which the reservoir is attached in order to hold the device in position in the uterine cavity.

This mode of administering contraceptive products makes it possible to use very low doses of progestative hormones, the latter being delivered directly to the target organ. The effectiveness of these devices is comparable to that of hormone-based contraceptives taken by mouth. Their duration of action is situated between two and five years and, unlike intrauterine devices comprising a copper wire instead of the reservoir, they are nonallergic. These hormonal intrauterine devices are used in particular in cases of hypermenorrhea, which frequently occurs with copper-based intrauterine devices.

The membrane surrounding the reservoir is formed from a silicone tube of small diameter and the thinnest possible wall. The technical constraints, however, do not make it possible to produce silicone tubes with a wall thickness of less than 0.4 millimeter and with a diameter of less than 1.5 millimeters. The diffusion of the hormone through the membrane must be slow, continuous and even, irrespective of the quantity of hormones present in the reservoir. This is possible, in application of Fick's laws on membrane diffusion, only for much thinner membranes.

Because of the maximal dimensions of the reservoir imposed by the morphology, it is known practice, for example from EP-A-0 652 738, to insert a cylinder of a product containing a hormone into a silicone tube. This insertion makes it possible to extend the silicone tube radially and, by stretching, to bring the wall of the tube to the desired thickness by exploiting the elastic properties of the silicone. In this method, a silicone tube is held in place and receives a blank in its opening. This blank comprises a means of injecting pressurized air which dilates the tube. Then, this blank is progressively replaced by a cylinder, made in advance, of product containing the hormone. The final step makes it possible to fixedly attach the membrane around the cylinder by reducing the air pressure inside the tube.

In the same spirit, U.S. Pat. No. 5,400,804 describes a method of making a tubular reservoir containing a contraceptive substance. A tubular reservoir, surrounded by a sheath, covers a needle placed in a mold. The needle injects air to increase the internal diameter of the reservoir. Once the diameter has been increased, a rod forming a support replaces the needle.

Such methods require the availability of a length of tube identical to the length of the cylinder of product. In other words, the latter must be made first and cut to the correct length; the same applies to the silicone tube. Furthermore, the injection of pressurized air may be inadequately controlled and/or the tube incorrectly held during this injection. It is then possible that, on the membrane of the tube, a bulge forms in which an air bubble is housed. Finally, such systems do not make it possible to effectively attach the external membrane to the internal cylinder.

It is these disadvantages that the invention intends more particularly to remedy by proposing a method and an item of equipment for making a reservoir containing an active substance into which a thin membrane is easily placed, while preventing the formation of a bulge on this membrane.

Accordingly, the subject of the invention is a method of making a reservoir containing an active substance and suitable for being inserted into a natural cavity of a living being, this reservoir comprising a membrane that is permeable to the active substance, characterized in that it comprises steps consisting in:

a) placing at least one tube designed to form this membrane in at least one retention member, the ends of the tube being open, b) injecting through one of the ends of the tube, while expelling all the residual air present in this tube, a quantity of a product containing an active substance in paste form, this quantity corresponding substantially to the internal free volume of the tube, c) when the tube is full, closing the end of the tube opposite to the end from which the injection is performed, d) continuing the injection of the product in paste form into the free volume of the tube until the desired external diameter for the reservoir is obtained by allowing the tube to expand radially, e) polymerizing the product when the reservoir has the desired external diameter while keeping the reservoir in the retention member.

Such a method makes it possible, in a single operation, to produce the reservoir and to fill it with active substance. It is no longer necessary to produce a cylinder of product separately. The injection of the product in the absence of air, under pressure, allows the latter to be evenly distributed in the tube while preventing the presence of bulges or air bubbles.

According to advantageous, but not mandatory, aspects of the invention, the method may incorporate one or more of the following features:

After step e), the reservoir is cut to the desired final. Length.

During step a), a rod is inserted into the internal volume of the tube.

During step a), several tubes are simultaneously placed in at least one retention member.

Steps b) to e) are carried out simultaneously on all the tubes placed in at least one retention member.

The invention also relates to an installation making it possible to apply a method as described hereinabove and, more specifically, an installation that comprises:

At least one member for the retention of at least one tube designed to form the membrane, at least one member for the injection of a product containing the active substance into the tube, at least one member for the closure of at least one end of the tube after it has been filled with the product.

Advantageously, the retention member comprises at least one mold defining a housing for receiving the tube when it is filled and when the product is polymerized.

The closure member comprises a rod and a plate for blanking off one end of the tube and one end of the housing.

The retention member is fitted, on an internal face, with coupling points of the wall of the tube suitable for preventing the retraction and/or the longitudinal extension of the wall when the product is injected and/or polymerized.

The rod is covered with a material not adhering to the rod, particularly a sheath.

The housing comprises at least one zone for receiving at least one member for positioning the ends of the tube.

The housing comprises two reception zones, each being placed in the vicinity of an end of the housing and suitable for receiving a positioning member.

These members are rings furnished with a radial collar.

These rings have an external diameter close to the external diameter desired for the reservoir.

The invention will be better understood and other advantages of the latter will appear more clearly on reading the following description of a method and of two embodiments of an installation according to the invention, given only as an example and made with reference to the appended drawings in which:

FIG. 1 is a view in perspective of a hormonal intrauterine device fitted with a reservoir made according to the invention, FIG. 2 is a view in perspective of the reservoir of the intrauterine device of FIG. 1, FIG. 3 is a view in perspective, on the same scale as FIG. 2, of an empty silicone tube designed to form the membrane surrounding the reservoir of FIG. 1, FIG. 4 is a schematic and longitudinal section, on another scale, of a first type of mold forming a means of retaining a silicone tube when the method is applied, FIG. 5 is a schematic, longitudinal section, on the same scale as FIG. 4, of a first means of injection of the product into the tube, FIGS. 6 to 10 are schematic, longitudinal sections illustrating the various steps of the method using the materials of FIGS. 4 and 5, and FIG. 11 is a schematic, lateral, longitudinal section of a second type of mold and of a means of injection of the product into the tube.

An intrauterine device 1 comprises a support 2 made of a polymer-based inert and nonallergic material. This support 2 is generally T-shaped with branches 3 curved in the direction of its rod 4, so as to be configured generally in the shape of a marine anchor. A reservoir 5 is positioned on the rod 4 of the support 2. The reservoir is configured as a cylinder with a circular base and provided with a central and longitudinal opening 6. The diameter $D_6$ of this opening is suitable for allowing the insertion with reduced clearance of the rod 4 into the reservoir 5. The reservoir 5 is immobilized in translation on the rod 4 by two bosses 70, 71 situated respectively in the vicinity of the ends of the rod 4. The terminal boss 70 of the rod 4 is furnished with an orifice 72 allowing threads to pass through making it easier to retract the intrauterine device from the uterine cavity.

The cylinder 5 comprises, in cross section, in addition to the central opening 6, an intermediate zone between the external wall of the reservoir and the opening 6. This zone, whose thickness lies generally between 1 mm and 2 mm, extends over the whole length of the reservoir 5. It is filled by a tube 8 of solid product. This solid product comprises approximately 20% to 40% of an active principle, particularly a progestative hormone, for example levonorgestrel. The quantity of hormone is sufficient to ensure that the device is effective for two to five years with a hormonal release of between 20 and 25 $\mu g/24$ hours which allows an effective contraceptive action. The rest of the product 8 consists essentially of silicone.

The external wall of the reservoir 5 is formed by a continuous membrane 9, thus producing a protective sleeve around the tube 8. Only the terminal sections of the cylinder 5 have no membrane. This membrane has a base of a silicone or a mixture of silicones. This or these silicones are advantageously of a type different from that entering into the composition of the product 8, particularly as concerns the silica filler.

As illustrated in FIGS. 2 and 3, the tubular membrane is formed from a tube 10 which has an internal diameter $D_{10}$ approximately two to three times smaller than the external diameter $D_8$ of the product 8. The thickness $E_{10}$ of its wall is greater than the thickness $E_5$ of the final membrane 9. The thickness of the wall is inversely proportional to the external diameter of the tube.

The radial extension of the tube 10 allows it to surround the product 8 forming the reservoir 5 of external diameter $D_5$, with a wall thickness $E_5$ thin enough to form a membrane. The elastic properties of the silicones and their porosity make it possible to satisfy the technical constraints evoked hereinabove. Other inert, nonallergic materials that are elastic, extendable, and permeable to the active substances can be used to produce a reservoir 5 via a method as described hereinafter.

As shown in FIG. 4, a first type of mold, in two separable parts, is made of a rigid but porous material, so as to allow humid air to pass between the interior and the exterior of the mold. Specifically, certain silicones polymerize in the presence of water; in this case, it is necessary to maintain a high relative humidity inside the mold. Advantageously, the mold is made of aluminum, or of an aluminum alloy, and provided with small orifices, for example of a diameter lying between 0.2 and 0.3 mm, regularly distributed over the mold. As a variant, the mold may be made of a sintered material or of compressed silica. The main portion 11 of the mold defines a central cylindrical housing 12 with a circular base and centered on an axis $X_{12}$. The internal diameter $D_{12}$ of the housing 12 is substantially identical to the final external diameter $D_5$ of the reservoir 5.

A rod 13, for example a metal rod, is positioned longitudinally in the housing 12, along the axis $X_{12}$. This rod has an external diameter $D_{13}$ corresponding substantially to the internal diameter of the finished reservoir 5, that is to say to the diameter $D_6$ of the opening 6. The rod 13 is fixedly attached, at one of its ends 13A, to a support or plate 14, generally in the shape of a disk, with a diameter $D_{14}$ greater than the diameter $D_{12}$. The rod 13, over its whole length, passes through the mold 11 without touching the walls of the housing 12. At one end, the housing 12 communicates through a convergent 12A with an orifice 15 having a smaller diameter than the diameter $D_{12}$.

The plate 14 is placed outside the mold 11, on the side of the outlet 12B of the housing 12 opposite the convergent 12A.

The orifice 15 allows the insertion of an end-piece of a first type of injection means represented schematically in FIG. 5. This injection means 16, generally syringe-shaped, comprises a main body 17 in which a piston 18 moves in a sealed manner. This piston 18 is hollow, in order to allow the rod 13 to pass through when the insertion end-piece 19 of the body 17 is in place in the orifice 15 of the mold 11. This injection device 16 is connected, where necessary, to a reserve of product so that it can operate continuously.

As shown in FIG. 6, the first step of the method of making the reservoir 5 consists in positioning, in the direction of the arrow $F_1$ in FIG. 6 and on the rod 13, the silicone tube or sleeve 10 after having inserted the end-piece 19, by force, into one end of the tube 10. Once the sleeve 10 covers the rod 13, the end-piece 19 of the injection system 16 is positioned in the mold as shown in FIG. 7.

A movement of the piston 18 in the direction of the other end 11A of the mold, according to the arrow $F_2$, moves the product 8 in paste form toward the annular space 20 lying between the rod 13 and the internal face of the tube 10. This product 8, which comprises the active principle, has a viscosity that varies according to the percentage of active principle. The viscosity of a silicone-based product is not measured directly. It is known practice, for silicones, to indirectly assess this viscosity by measuring the speed of flow of the product under a given pressure. One method used is given by the American standard ASTM-033 in which the speed of flow is expressed in grams per minute. In this instance, the product 8 has a speed of flow greater than 2 grams per minute and preferably lying between 2.8 and 3 grams per minute. As a variant, the injection is made by an endless screw or a membrane system.

The product 8 is injected slowly, steadily and continuously for example under the action of an electric, pneumatic or mechanical force exerted on the piston 18. The quantity injected is determined in order to substantially fill the annular volume 20 available in the silicone tube 10 thus retained in the housing 12. This injection takes place without notable radial and/or longitudinal deformation of the tube 10, because of the quantity injected and the speed of injection. Furthermore, the mold holds the tube 10 in place.

As shown in FIGS. 7 and 8, the end 21 of the tube 10, opposite the orifice 15 remains open throughout the period of injection of the product 8. Once the tube 10 has been filled, the filling being made easier by the opening of the end 21, which allows all the residual air to be expelled from the volume 20, the piston 18 is still not abutting against the end-piece 19 inserted in the end of the mold fitted with the orifice 15, because of the quantity of product 8 initially present in the device 16 as shown in FIG. 8.

During this step, the tube 10 is entirely filled by the product 8, except for the volume occupied by the rod 13. The product is uniformly distributed in the annular space 20. It is particularly free of air bubbles in the vicinity of the wall of the tube 10.

In the next step, illustrated in FIG. 9, the end 21 of the tube 10 is blanked off by the plate 14 because of its movement in the direction of the arrow F.sub.3 by sliding along the rod 13. The plate 14 then closes the outlet 12B and the end 21 of the tube 10. Only a passage for the rod 13: is preserved in the closure system. The rod 13 is immobilized, for example, by a jaw device, a guillotine valve device. As a variant, not shown, the end 21 and the outlet 12B are closed by a guillotine or pincer system. This blanking off of the end 21 being carried out, the product 8 can no longer be expelled through this end of the tube 10 opposite to the syringe 16. The injection of the product 8 into the tube 10 in the direction of the arrow F.sub.4 continues. This second injection takes place under a greater pressure than the first. Because of the elastic properties of the wall 9 of the silicone tube 10, the latter dilates radially in the direction of the arrows F.sub.5 and F'.sub.5 until coming into contact with the internal face 11A of the mold 11 which defines the housing 12. Because the pressure exerted by the product 8 on the wall 9 is constant and uniformly distributed on this wall 9, the tube 10 is dilated while preventing any bulge and while producing a wall 9 whose final thickness is even at all points of the wall. This forms a membrane whose porosity and diffusion coefficient are optimal and even. The quantity of product 8 injected during this step is particularly a function of the final diameter D.sub.5 of the reservoir 5, that is to say, in practice, a function of the internal diameter D.sub.12 of the housing 12.

The injection is terminated when the external face of the wall 9 of the tube 10 and the internal face 11A of the mold 11 are in contact over the whole of their respective surface.

It is then appropriate to await the polymerization of the product in the tube 10. The polymerization of a silicone-based product on an element itself made of silicone allows an effective connection between the components, in a manner similar to a weld. The porosity, at the same time of the wall 9 and of the material forming the mold 11, makes it possible to maintain in the mold enough relative humidity to ensure a rapid and complete polymerization of the product B. This produces a reservoir 5 in which the product 8 is effectively retained and evenly distributed in the membrane 9, which improves the hormonal diffusion.

In order to prevent any retraction and/or longitudinal extension during the injection of the product 8, the internal face 11A is not smooth but has asperities, not shown, sufficiently large to form coupling points of the wall 9 of the tube 10 thus preventing its retraction and/or its longitudinal extension during the injection of the product 8 and/or the polymerization.

If necessary, a pause in the injection is made to leave time for the tube 10 to resume its initial longitudinal dimensions.

In this way, the production of the product 8 and its insertion into the reservoir 5 are achieved in a single operation.

In a final step, not shown, the rod 13 is withdrawn from the mold 11 in the direction of the arrow F.sub.6 in FIG. 10, which allows the reservoir 5 to be extracted from the housing 12. The rod may then be extracted from the reservoir.

At the time of polymerization, an adhesion of the product 8 on the rod 13 may compromise an easy retraction of the latter from the mold 11.

To prevent this adhesion, the rod 13 is covered with a material that does not adhere to the rod 13. Advantageously, it is a sheath 130. This thin sheath 130 is made of a material that is biocompatible and inert relative to the other components of the intrauterine device 1.

This sheath 130 is positioned on the rod 13 prior to the latter being installed in the mold 11.

In addition to an easy retraction of the rod 13, this sheath 130 helps the seal between the ends of the rod 13 with the piston 18 and the plate 14.

As a variant, the sheath 130 is replaced by a surface coating of the rod 13 that does not adhere to the product 8. In another embodiment, the material forming the rod 13 itself does not adhere to the product 8.

According to one aspect, not shown, of the invention, the mold 11 may be formed of two matching half-shells together defining the housing 12. In this case, after the polymerization, the mold is opened to allow the retraction of the reservoir 5.

When the rod 13 has been withdrawn, the aforementioned assembly is cut to the desired length as a function of the length of the rod 4 that is then inserted into the opening 6. In practice, the length of the housing 12 may make it possible to produce several reservoirs 5 end-to-end.

In a variant, not shown, the mold 11 comprises several grooves 12 placed in parallel and/or in a star shape, thus allowing the simultaneous and parallel production of several reservoirs. The injection device 16 is adapted accordingly.

As a variant, the injection device 16 is fitted with a means of continuously supplying the main body 17 with the product 8.

In another embodiment, the mold 11 has no rod similar to the rod 13. The reservoir obtained is a full cylinder. It is then necessary to produce a support different from that previously described. This may be, for example, a support fitted with open ring type coupling means.

As a variant, the installation comprises a mold 11 whereof the length of the housing 12 is shorter than that described. These molds are suitable for receiving, instead of the central rod 13, the rod 4 of a support 2. In this case, the hormonal intrauterine device is produced, in a single operation ready for use, by overmolding the reservoir 5 onto the rod 4. In this case, the length of the housing 12 corresponds substantially to the length of the intrauterine device 1, the cutting step being no longer necessary.

FIG. 11 illustrates another type of mold and another means of injecting the product according to the invention. This other mold 22 comprises a bottom half-mold 23 and a top half-mold 24. The mold 22 is made of a material similar to that of the mold 11 in order to allow the retention of a high relative humidity in the mold.

The bottom half-mold 23 comprises a central housing 25A of dimensions and shape adapted to the desired dimensions of the reservoir 5. In this instance, the housing 25A is semicylindtical with a circular base. In the vicinity of the ends of this housing 25A, cut-outs 26 are made.

The end sections of the half-mold 23 are fitted, in the top portion, with a groove 27. These grooves 27 have a shape and dimensions suitable for receiving the rod 13.

The top half-mold 24 is similar to the half-mold 23. It comprises a semicylindrical central housing 25B with a circular base. This housing 25B, similar to the housing 25A, has dimensions and a shape adapted to the desired dimensions of the reservoir 5. In particular, the half-mold 24 is fitted with grooves 27 and cut-outs 26 of shapes and dimensions similar to those of the half-mold 23. The cut-outs 26 and the grooves 27 of each half-mold 23, 24 are advantageously placed facing one another when the mold 22 is closed. In this configuration, the mold 22 comprises a central housing 25 formed by the housings 25A and 25B of the half-molds 23 and 24.

The half-mold 24 is provided with two orifices 28, 29 placed in the vicinity of its ends. These orifices 28, 29 are perpendicular to a longitudinal axis $X_{25}$ of the housing 25B when the mold is closed. They allow a communication between the outside of the mold 22 and the housing 25 when the mold is closed.

The orifice 28 is a through-orifice and opens into the housing 25B, between a cut-out 26 and the end wall 25C of the housing 25B. The external outlet of this orifice has an internal diameter close to the external diameter of the end-piece 19 of a syringe 16.

The orifice 29 made on the other end of the half-mold 24 forms a blind compartment. This orifice is traversed, in the vicinity of its closed end, by a channel 30. This channel is oriented in a direction generally parallel to the axis $X_{25}$ when the mold is closed. The channel 30 connects the outside and the housing 25. This channel 30 receives a stopping member 31, for example a pin made of rigid polymer. This pin 31 can be moved in the channel 30 in order to stop the latter and prevent, any communication, via the channel 30 or the orifice 29, between the housing 25 and the outside.

The orifice 28 is also traversed by a channel 32 in which a stopping member 33 in the form of a pin moves. This channel 32 is blind, its closed end being situated in the wall of the half-mold 24. It is placed in the vicinity of the outlet of the orifice 28. The channel 32 is oriented parallel to the axis $X_{25}$ when the mold is closed.

These stopping members 31, 33 have a length and a diameter that are sufficient to stop the corresponding channels 30, 32 in a sealed manner.

When it is desired to produce an intrauterine device 1, the user inserts, at each end of a tube 10, for example by means of a spreader-type plier, a positioning member 34. This member is formed by a ring 34 made of a rigid, inert and biocompatible material. This ring 34 is fitted with a radial collar 35 extending outward. The internal diameter $D_{34}$ of the ring 34 is close to the desired external diameter $D_5$ of the reservoir 5. Thus the ends of the tube 10 covering the rings 34 have a diameter close to their final diameter when the reservoir 5 is produced. The rod 13, also covered by a sheath 130 similar to that mentioned hereinabove, is then inserted into the opening of the tube 10. The assembly is then positioned in the bottom half-mold 23, so that the ends of the rod 13 rest in the grooves 27. The tube 10 is positioned in the half-mold 23 so that the collars 35 of the end rings 34 are inserted, with reduced clearance, into the corresponding cut-outs 26.

The mold 22 is closed by folding down the top half-mold 24. Thus, the grooves 27 and the cut-outs 26 of the half-mold 24 cover the free portions of the rod 13 and of the collars 35. Thus the tube 10 and the rod 13 are retained and positioned exactly in the mold 22.

In a first step, similar to that previously described, the product 8 in paste form is injected through the orifice 28 after the end-piece 19 of a syringe has been inserted into the outlet of the latter. The pin 33 is in the retracted position in order to allow the product to pass into the housings 25A and 25B. The product 8 enters the tube 10. The air contained in the tube 10 is expelled from the mold 22 and exits via the orifice 29 whose passage is free, the pin 31 being in the retracted position.

When the paste product 8 occupies all the available space between the concentric tube 10 and sheath 130, the orifice 29 is stopped by pushing the pin 31 in the direction of the housing 25B. The injection of the product 8 is then continued until the desired diameter of the reservoir 5 is obtained. During the injection, the tube 10 is held in place by the rings 34. There may therefore be no longitudinal expansion of the tube 10; only radial expansion is permitted. At the end of the operation, the injection orifice 28 is stopped by pushing the pin 33 to the end of the channel 32.

The polymerization takes place in a humid environment in a manner similar to that previously described. At the end of the method, the mold is opened and the rod 13 which slides freely inside the sheath 130 is easily withdrawn. The reservoir is cut to the desired length. This cut is made particularly at the rings 34.

As a variant, the user places several molds, 22 in parallel, supplied by a syringe-type device with multiple end-pieces in order to produce several reservoirs 5 in parallel.

The invention claimed is:

1. A method of making a reservoir (5) containing an active substance and suitable for being inserted into a natural cavity of a living being, said reservoir (5) comprising a membrane (9) that is permeable to said active substance, characterized in that it comprises:
   a) placing at least one tube (10) designed to form said membrane in at least one retention member (11; 22), the ends of said tube being open,
   b) injecting (16) through one of said ends of said tube (10), while expelling all the residual air present in said tube, a quantity of product (8) containing an active substance in paste form,
   c) when said tube (10) is full, closing the end (24) of the tube opposite to the end from which the injection (16) is performed,
   d) continuing the injection (16) of said product (8) in paste form into said free volume (20) until a pre-determined external diameter ($D_5$) for said reservoir (5) is obtained by allowing said tube to expand radially ($F_5$, $F'_5$), and
   e) polymerizing said product (8) when the reservoir (5) has the pre-determined external diameter ($D_5$) while keeping the reservoir (5) in the retention member (11; 22).

2. The method as claimed in claim 1, characterized in that, after step e), the reservoir (5) is cut to a pre-determined final length.

3. The method as claimed in claim 1, characterized in that, during step a), a rod (13) is inserted into the internal volume (20) of said tube (10).

4. The method as claimed in claim 1, characterized in that, during step a), several tubes (10) are simultaneously placed in at least one retention member.

5. The method as claimed in claim 4, characterized in that steps b) to e) are carried out simultaneously on all the tubes (10) placed in at least one retention member.

\* \* \* \* \*